United States Patent [19]
Gordon et al.

[11] Patent Number: 4,845,472
[45] Date of Patent: Jul. 4, 1989

[54] LEAK SENSING ALARM AND SUPPLY SHUT-OFF APPARATUS

[75] Inventors: Harris K. Gordon, Elkins Park, Pa.; Howard Myers, Parlin, N.J.; Robert Pasquarello, Glenmoore, Pa.

[73] Assignee: HKG Industries, Inc., Rydal, Pa.

[21] Appl. No.: 928,075

[22] Filed: Nov. 6, 1986

[51] Int. Cl.⁴ ............................................. G08B 21/00
[52] U.S. Cl. ..................... 340/605; 340/604; 340/691; 200/61.04
[58] Field of Search ............... 340/604, 605, 620, 691, 340/618, 619, 623–625; 200/61.04, 61.05; 73/290 R, 304 R

[56] References Cited

U.S. PATENT DOCUMENTS

| 2,552,088 | 5/1981 | Davis | 340/604 |
|---|---|---|---|
| 3,438,246 | 4/1969 | Lotti | 340/605 |
| 3,771,548 | 11/1973 | Rauchwerger | 73/304 |
| 4,223,692 | 9/1980 | Perry | 340/628 X |
| 4,297,686 | 10/1981 | Tom | 340/604 |
| 4,324,268 | 4/1982 | Jacobson | 340/620 X |
| 4,374,379 | 2/1983 | Dennison, Jr. | 340/604 |
| 4,596,980 | 6/1986 | Bergeron et al. | 340/626 |

FOREIGN PATENT DOCUMENTS 2923536 12/1980 Fed. Rep. of Germany ...... 340/604

Primary Examiner—Joseph A. Orsino
Assistant Examiner—Jeffery A. Hofsass
Attorney, Agent, or Firm—Robert C. Podwil

[57] ABSTRACT

Apparatus for sensing the presence, in an area served by a water supply line, of unwanted water indicative of a malfunction. The apparatus responds to the sensing of water by operating a remote solenoid-actuated valve, to shut off the water supply. Three operative conditions of the apparatus, "standby", "alarm" and "manual remote shut off", are provided, enabling an operator to selectively actuate the valve independently of the sensor.

9 Claims, 2 Drawing Sheets

U.S. Patent  Jul. 4, 1989  Sheet 1 of 2  4,845,472
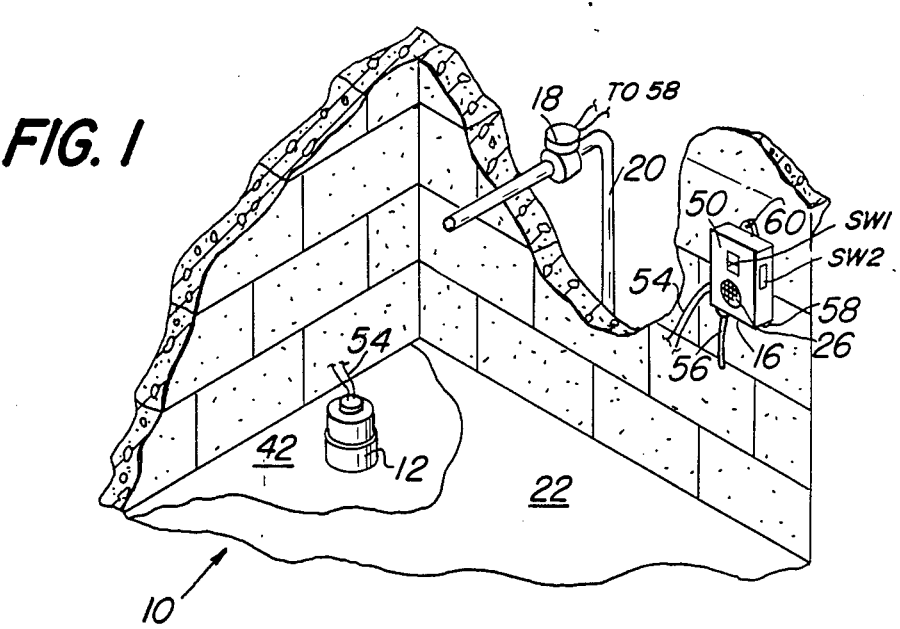
FIG. 1
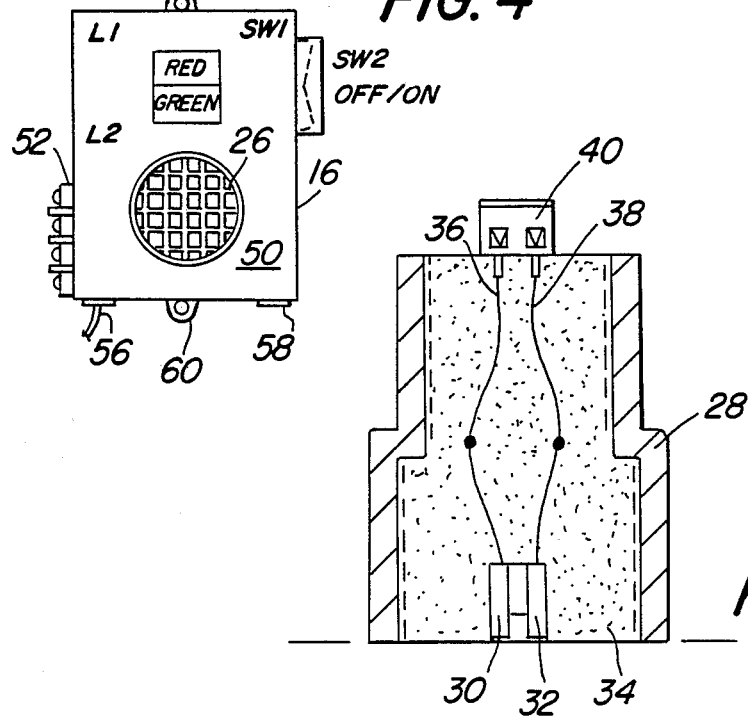
FIG. 4
FIG. 2

LEAK SENSING ALARM AND SUPPLY SHUT-OFF APPARATUS

BACKGROUND OF THE INVENTION

This invention relates to a leak sensing alarm and supply shut-off apparatus, and more particularly, to apparatus which, operating on available house current, senses the presence in an area served by a water supply line of unwanted water, indicative of a malfunction or "fault" condition.

Water service lines, like other utilities, frequently are made to enter houses or other enclosures in areas in which they are not subject to constant observation. For example, in dwellings, it is conventional for the water supply line to emerge in a basement, crawl space or utility space, locations at which system faults, revealed by water leakage, are not readily be observed by users or inhabitants. It is also true, of course, that water leakage anywhere in a structure is a dwelling, which may be caused by the failure of a plumbing fixture or pipe, may eventually find its way to the lowest point in the structure, where its presence may be observed or otherwise detected. Areas at which leaked water accumulates are only rarely subject to constant observation.

SUMMARY OF THE INVENTION

The present invention provides, therefore, apparatus of remotely sensing the presence, in an enclosure or area served by a water supply line, of standing water indicative of a fault or malfunction.

In accordance with the invention, the supply line is provided with a solenoid-actuated cut-off valve, which is preferably made operable by AC line current. The apparatus provides a means whereby the cut-off valve may automatically be operated in response to a sensed "fault" condition or, if desired, manually closed by a remote cut-off switch which enables a user to actuate the valve independently of the apparatus and its sensor. The apparatus may also be left in an active "STAND-BY" condition, in which the cut-off valve is open, but the apparatus is so configured that the cut-off valve will close in response to a sensed fault.

In general, the apparatus comprises a control circuit so arranged that an operator may select the "STAND-BY" configuration, a manual remote cut-off condition, or a manual bypass of the apparatus, wherein the cut-off valve is left in its open condition.

The apparatus provides to the user a switch which enables the user to bypass the apparatus by placing the cut-off valve in an open condition, and in effect shunting around the control circuitry of the apparatus. Assuming, however, that this switch, in effect a disarming switch, is not used, the apparatus provides three normal modes of operation: (a) "STAND-BY" mode, in which the apparatus is armed and prepared to sense a fault, (b) "ALARM" mode, in which the apparatus senses a fault, and (c) "MANUAL REMOTE SHUT-OFF" mode, in which the actuation of a selectively controlled switch causes the cut-off valve to remain in its closed state, thus cutting off the water supply to the protected area.

A control panel may be provided at any convenient location, and on the panel there may be provided the above-mentioned "on-off" switch and a pair of indicator lights signifying the mode or condition of the apparatus at any given time. A green indicator light preferably signifies the STAND-BY mode, a red indicator light signifies the "ALARM" mode. Both the red and green indicator lights are illuminated when the apparatus is in the MANUAL REMOTE SHUT-OFF mode. An audible alarm is also provided to give an indication that the apparatus is in the "ALARM" mode.

In the presently preferred form of the apparatus, a transformer-coupled power supply provides approximately 13 Volts DC to the control circuitry. In the "STAND-BY" mode the output of a comparator is in a "low" logic state, and enables the lighting of the green indicator while causing the red indicator and the alarm to be inoperative. Sensing, however, of a fault condition, provides an input to the comparator which causes a change of state, disabling the green indicator and enabling driving of the alarm. A string of driver stages, normally disabled in the "STAND-BY" mode, are also caused, when a fault is sensed, to drive the red indicator light.

A relay serves to reset the circuitry for sensing (the "STAND-BY" mode) when a fault has been cleared and it is desired that the apparatus once again placed in the STAND-BY mode.

There is seen in the drawings a form of the invention which is presently preferred (and which represents the best mode contemplated for carrying the invention into effect), but it should be understood that the invention is not limited to the precise arrangements and instrumentalities shown or described herein.

BRIEF DESCRIPTION OF DRAWINGS

FIG. 1 is a pictorial view, showing apparatus in accordance with the present invention in a hypothetical installation;

FIG. 2 is a detailed view, in cross-section, showing a detector element as used in the present invention;

FIG. 4 is a front elevation view of a control panel for use with the invention.

DETAILED DESCRIPTION

Figure 3:
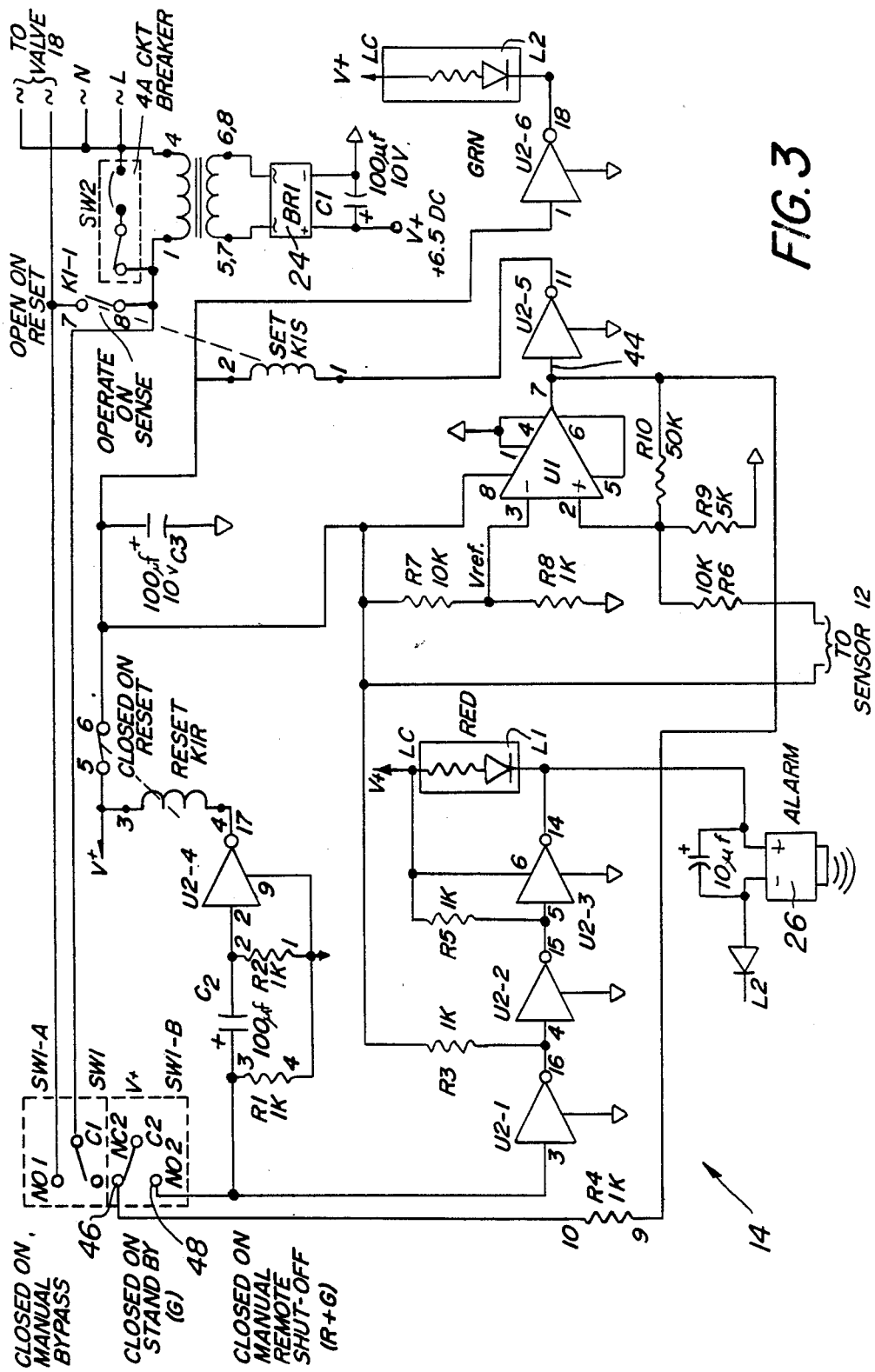
FIG. 3 is a circuit diagram of a presently preferred embodiment of the invention.

Referring now to the drawings in detail, wherein like reference numerals indicate like elements, there is seen in FIG. 1, a leak sensing alarm and supply shut-off apparatus, designated generally by the reference numeral 10.

In general, the apparatus 10 comprises a sensing element, or detector 12, operatively coupled, in a manner described in greater detail below, to control circuitry (not seen in FIG. 1 but described in detail in reference to FIG. 3), disposed within a console or control box 16.

Responsive to the control circuitry 14 or, as will be seen, to a manual over-ride switch/circuit breaker SW2 for the control circuitry 14, is a solenoid-actuated cut-off valve 18, associated with the main water supply line 20 to the protected area or premises 22.

Referring now to FIG. 3, a power supply, designated generally by the reference numeral 24, is provided. The power supply 24 is preferably a conventional transformer-coupled, full-wave bridge power supply with a capacitive input filter, configured to apply approximately 13 Volts DC to the control circuitry 14.

For purposes of description, the normal conditions, or modes, of operation of the circuitry 14 may be referred to as "STAND-BY", "ALARM" and "MANUAL REMOTE SHUT-OFF", respectively.

In the "STAND-BY" mode, only a green panel indicator L2 (seen also in FIG. 4) is illuminated, and the control circuitry of the apparatus 10 is armed and ready to sense a "fault" condition.

The control circuitry 14 is placed in the "ALARM" mode when a "fault", characterized by the presence of water indicative of a leak, is detected. The "ALARM" mode is indicated to a user by the illumination of a red panel indicator L1 and the sounding of an audible alarm 26, and by the operation of the solenoid-actuated valve 18 to cut off the water supply.

The "MANUAL REMOTE SHUT-OFF" mode may be selected by the user, to place the solenoid-actuated valve 18 in the cut-off state, even if a "fault" condition which would otherwise trigger the "ALARM" mode is absent. The "MANUAL REMOTE SHUT-OFF" condition is signified by the illumination of both the red L1 and green L2 panel indicators, and by the absence of an audible alarm signal.

An "ON-OFF" switch SW2 is provided, preferably on the control box 16, if the device 10 should fail, or if the user should wish to bypass the apparatus 10 for any reason. The switch SW2 bypasses all of the control functions of the apparatus 10, and leaves the solenoid-actuated valve 18 in its open condition. For the purposes of the following description, it will be assumed that the switch SW2 is at all times in its "ON" state.

Referring again to FIG. 3, the apparatus is seen in the "STAND-BY" mode. A two-section manual bypass switch SW1, with sections designated SW1-A and SW1-B has its section SW1-A in the "OFF" (deenergized) state, in which its contacts are open, and relay contacts K1-1 associated with the solenoid-actuated valve 18 are also open, thereby disabling the solenoid-actuated valve 18. The relay K1 is a dual coil latching relay, with complementary switch K1-1 and K1-2.

Section SW1-B of the switch SW-1 serves to select the operating condition or mode of the apparatus 10, and in the "STAND-BY" mode, supplies power (V+) to detection circuitry consisting of a comparator U1 and driver stages U2-5 and U2-6. In the absence of a "fault" signal at the sensor 12, the comparator U1 is in its quiescent (logic "low") state. In this state, the input voltage at U1 pin 2 is lower than the reference voltage at U1 pin 3, the latter being supplied through the resistance network R7, R8 at 1.2 Volts DC. With the circuit thus configured, the output of the comparator U1 is forced to ground, sinking the current supplied through the load resister R4, and providing no current source to the driver stage U2-5. The driver stage U2-5, it will be seen, drives set coil K1-S of the relay K1. These, when as here, the contacts K1-1 are open, their complements, contacts K1-2, are closed. A green indicator L2 is driven from the driver stage U2-6, which receives its source current from V+ via relay contacts K1-2.

The comparator U1 may comprise a Texas Instruments Co. No. LM311N or equivalent integrated circuit comparator. U2 may comprise a Sprague Electric integrated circuit transistor array No. ULN 2804A or equivalent.

Referring now to FIG. 2, the sensor 12 comprises a housing 28, preferably of PVC plastic within which are disposed a pair of carbon rod electrodes 30, 32, supported by an insulating medium 34, such as epoxy "potting" material. Conductors 36, 38 connect the electrodes 30, 32 to a terminal block 40, which couples the sensor 12 to the control circuitry 14.

The face of the sensor 12 is smoothed during manufacture to insure exposure of the electrodes 30, 32 and to provide a smooth surface for mounting. Under normal, dry conditions, the sensor is, functionally, an open circuit, allowing no current to pass between its electrodes 30, 32. If, however, the face of the sensor 12 becomes wet, a current path forms between the electrodes 30, 32, which enables a voltage to be impressed on the input of the detector circuitry. In other words, the presence of a fault condition, such as the leaked water 42 seen in FIG. 1, causes the sensor 12 to become a conductive element in the control circuitry 14, and the conductive condition of the sensor 12 provides a fault signal for the control circuitry 14.

Referring again to FIG. 3, when the sensor 12 becomes conductive, thus providing a fault signal, current is allowed to flow from V+ to the non-inverting input of U1, at pin 3. In the illustrated circuit, should the conductivity of the sensor 12 be sufficient to allow a current of greater than 250 microamperes, the voltage impressed at the input of the comparator U1 pin 2 will be greater than that of the reference at pin 3, causing the output of the comparator U1 to change state. When this occurs, current supplied through R4 serves as a source for the driver stage U2-5, which in turn energizes the set coil K1-S of the relay K1, and causes the contacts K1-1 and K1-2 to change their respective states.

When the contacts K1-1 move from the open to the closed state, they complete a circuit from L to the solenoid-actuated valve 18, and cause the valve 18 to close. At the same time, the complimentary contacts K1-2 of the relay K1 open and remove power (V+) from the comparator U1, thereby preventing the control circuitry 14 from automatically resetting when the fault is cleared.

When the contacts K1-1 and K1-2 of the relay K1 transfer, the source current is also removed from the driver stage U2-6 for the green indicator L2, thus extinguishing the green indicator L2. Finally, V+ is also removed from a bias resistor R3, which eliminates the bias from a driver stage U2-2 pin 4. With the removal of this bias, the output pin 15 of the driver stage U2-2 no longer conducts current to ground, and permits the input of the next driver stage U2-3 to be biased "ON", thereby causing its output to conduct current to ground and enabling illumination of the red indicator L1. The circuit for the audible alarm 26 is connected between the driver stage U2-3 pin 14 and the driver stage U2-6 pin 18. Therefore, when the output of the driver stage U2-3 is "low" and the output of the driver stage U2-6 is "high", the audible alarm 26 will also be active. It will be seen that no other combinations of output states on driver stage U2-3 pin 14 and driver stage U2-6 pin 18 will cause the audible alarm 26 to operate.

Once the fault condition has been cleared, the control circuitry 14 may be placed in the "REMOTE MANUAL SHUT-OFF" mode by depressing the switch SW1 once. This causes transfer of the contacts of the manual bypass switch SW1-A and the remaining section SW1-B of the switch SW1. When the common contact of the section SW1-B moves from the normally closed contact 46 to the normally open contact 48, the supply voltage is removed from the resistor R4. This, it will be seen, eliminates the bias on the input of the driver stage U2-5 which drives the "set" coil of the relay K-1, and forces the driver stage U2-5 output "off", thus deenergizing the set coil K1-S. Upon closure of the normally open 48 contact of the switch section SW1-B, current flows to the input of the driver stage U2-4 for the reset coil K1-R of the relay K1 until a coupling capacitor C2 charges to V+. This transient current forces the driver stage U2-4 into conduction, and energizes the reset coil K1-R. With the reset coil K1-R active, the relay contacts K1-1 and K1-2 toggle to their alternate states.

It will be seen that opening of the relay contacts K1-2 breaks one circuit between the AC supply line and the solenoid-actuated valve 18, but no change in operation results because the contacts of the manual bypass switch SW1-A, closed when SW1 was depressed, maintain this circuit. The remaining relay contact K1-1, now closed, supplies power to the comparator U1, the driver stage U2-5 for the set coil K15, and the driver U2-6 for the green indicator L2. V+ is also reapplied to the driver stages U2-1, U2-2 and U2-3 for the red indicator L1, which causes the output driver stage U2-3 to conduct and illuminate the red indicator L1. With both indicators on, the user is visually warned that the unit is in the "MANUAL REMOTE SHUT-OFF" mode, and that the solenoid-actuated valve 18 is closed.

Referring now to FIG. 4, there is seen an exemplary control panel, designated generally by the reference 50. Seen on the panel 50 are the red and green indicators L1, L2 which may be made integral with the switch SW1. Also associated with the panel 50 (or the control box 16 with which the panel 50 is associated) are the switches SW1 and SW2, preferably labeled to indicate their respective functions.

The alarm 26, and control circuitry 14 (not seen in FIG. 4) may be housed in the control box 16. The control box 16 also provides external connections 52 for wiring 54 associated with the sensor 12 (and other sensors, if any). A line cord 56 may be provided to supply line power to the apparatus 10, and an A.C. outlet port 58 may also be provided. Mounting tabs 60 may also be provided, to facilitate mounting of the control box 16 on a wall or other convenient mounting point.

The present invention may be embodied in other specific forms without departing from its spirit or essential attributes. Accordingly, reference should be made to the appended claims, rather than the foregoing specification, as an indication of the scope of the invention.

We claim:

1. For use with a liquid supply line having a cutoff valve associated therewith, apparatus comprising a detector for detecting the presence of leaked moisture indicative of a fault condition; an actuator coupled to said cutoff valve and detector and operable to actuate said cutoff valve to an "off" position in response to a fault condition; first visible condition indicator means for indicating that the apparatus is in an armed state; second visible condition indicator means for indicating that the detector senses a fault condition, said second condition indicator means being responsive to said detector; electronic circuit means operatively interconnecting said first and said second condition indicator means, whereby sensing of a fault condition deactivates said first condition indicator means and activates said second condition indicator means; and a manually operable switch for selectively manually operating said cutoff valve, said manually operable switch being operatively coupled to said first and second condition indicator means to activate both said first and second condition indicator means when said manually operable switch is in a closed condition so as to indicate the condition of said manually operable switch.

2. Apparatus in accordance with claim 1, wherein said first and second condition indicator means comprise lights of different colors.

3. Apparatus in accordance with claim 2, wherein said first and second condition indicator means are disposed in said manually operable switch.

4. Apparatus in accordance with claim 3, and a second manually operable switch means operatively associated with said electronic circuit means, said second manually operable switch means being selectively operable to bypass said electronic circuit means to render said apparatus inoperative.

5. For use with a liquid supply line having a cutoff valve associated therewith, apparatus comprising a detector for detecting the presence of leaked moisture indicative of a fault condition; an actuator coupled to the cutoff valve; switch means responsive to said detector for energizing said actuator to close the cutoff valve in response to detection of a fault condition a manually operable switch for manually remotely operating the cutoff valve independently of said switch means; first condition indicator means for indicating that the apparatus is in an armed state; second condition indicator means for indicating detection of a fault condition; said second condition indicator means being operatively coupled to and responsive to said detector; and electronic circuit means operatively interconnecting said detector and said first and said second conditioner indicator means so that sensing a fault condition deactivates said first condition indicator means and activates said second indicator means, said first and second condition indicator means being disposed in said manually operable switch.

6. Apparatus in accordance with claim 5 wherein said manually operable switch is operatively coupled to said first and second indicator means, to activate both said first and said second condition indicator means when said manually operable switch is in a closed condition.

7. Apparatus in accordance with claim 6 and an audible fault alarm responsive to said detector.

8. Apparatus in accordance with claim 5, wherein said detector comprises a comparator and a sensor element operatively associated with said comparator, said sensor element being conductive in the presence of leaked moisture, said sensor element and comparator being so connected that sensing of a fault condition enables an output current of said comparator, said sensor element and said second condition indicator being so connected that sensing of a fault condition enables illumination of said second condition indicator, a relay electrically coupled to the output of said comparator and controlled thereby, said relay having first and second relay contacts, said first relay contacts deactivating said detector and said first indicator means upon sensing of a fault condition and said second relay contacts energizing said actuator to close the cutoff valve upon sensing of a fault condition, said switch means responsive to said detector for energizing said actuator being said second relay contacts; and said relay having a reset coil, and means responsive to said manually operable switch for actuating said reset coil.

9. Apparatus in accordance with claim 8, wherein said sensor element and said second condition indicator are so connected that sensing of a fault condition enables illumination of said second condition indicator; and an audible fault alarm responsive to said detector, said alarm being operative when said first condition indicator is inactive and said sensor element is conductive.

* * * * *